United States Patent [19]

Szwarc

[11] Patent Number: 4,613,326
[45] Date of Patent: Sep. 23, 1986

[54] TWO-COMPONENT MEDICATION SYRINGE ASSEMBLY

[75] Inventor: Joseph M. Szwarc, Cedar Grove, N.J.

[73] Assignee: Becton, Dickinson and Company, Franklin Lakes, N.J.

[21] Appl. No.: 754,801

[22] Filed: Jul. 12, 1985

[51] Int. Cl.$^4$ ............................................. A61M 37/00
[52] U.S. Cl. ...................................... 604/89; 604/218; 604/238
[58] Field of Search ................. 604/191, 238, 90, 187, 604/218, 89, 222

[56] References Cited

U.S. PATENT DOCUMENTS

| | | | |
|---|---|---|---|
| 2,591,046 | 4/1952 | Brown | 604/90 |
| 2,717,601 | 9/1955 | Brown | 604/90 |
| 3,330,282 | 7/1967 | Visser et al. | 604/90 |
| 3,828,980 | 8/1974 | Creighton et al. | 604/191 |
| 4,030,498 | 6/1977 | Tompkins | 604/222 |
| 4,235,235 | 11/1980 | Bekkering | 604/238 |
| 4,469,482 | 9/1984 | Lissenburg et al. | 604/238 X |

Primary Examiner—John D. Yasko
Attorney, Agent, or Firm—John L. Voellmicke

[57] ABSTRACT

A two-component syringe assembly includes an elongate barrel having a chamber for retaining fluid and a distal end having a passageway therethrough communicating with the chamber. A bypass stopper is slidably positioned in fluid-tight engagement inside the barrel. The barrel also includes a bypass defining a bypass zone positioned along the barrel for allowing fluid to flow around the bypass stopper when the bypass stopper is positioned intermediate the ends of the barrel in the bypass zone. A stopper is slidably positioned in fluid-tight engagement inside the barrel. A rigid plunger rod having an elongate body portion engages the stopper to facilitate its operation. A barrier flange is positioned on the body portion and intermediate the ends thereof. The barrier flange projects outwardly from the body portion into the space between the inside wall of the barrel and the outside of the body portion for acting as a barrier for blocking the path of fluid which may be propelled in a distal direction through the bypass when the syringe is being operated. The area described by the barrier flange as viewed along the longitudinal axis of the plunger rod is at least about 87 percent as large as the area described by the interior of the barrel as viewed along the longitudinal axis of the barrel.

28 Claims, 28 Drawing Figures

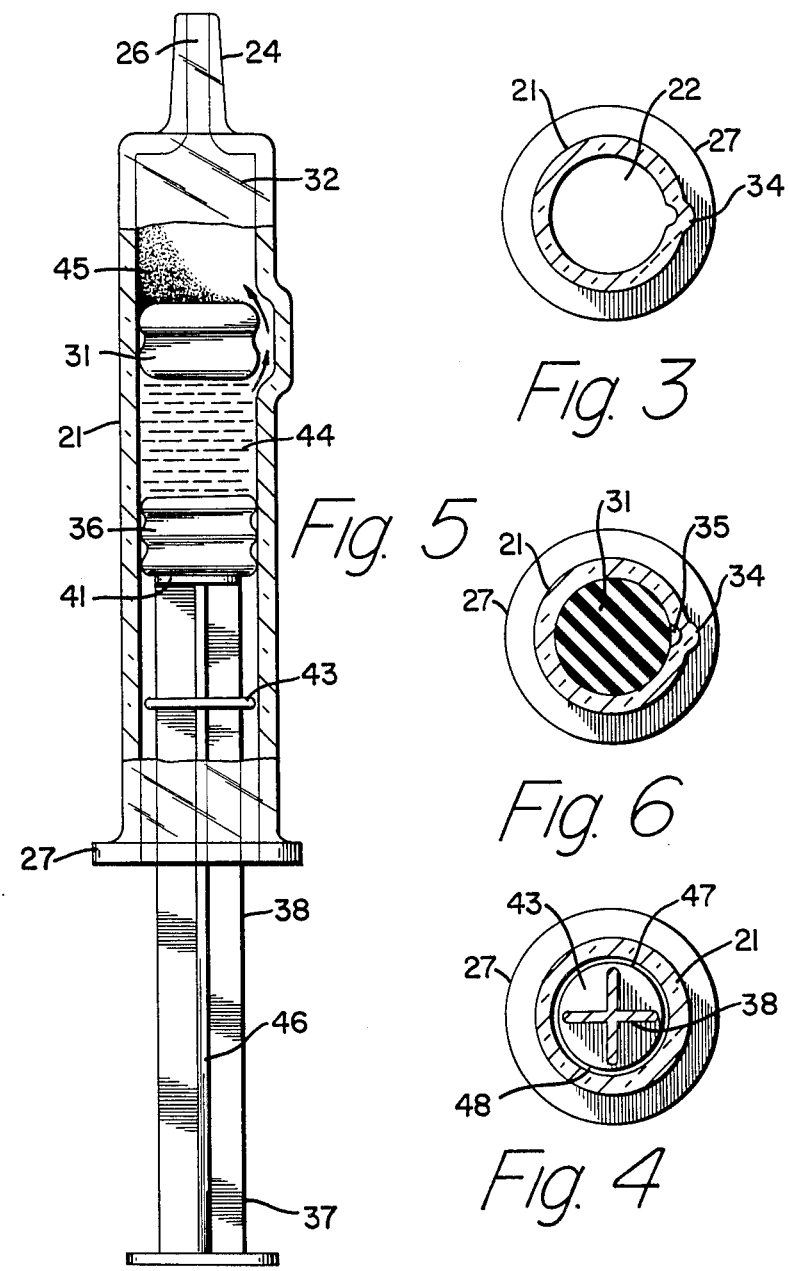

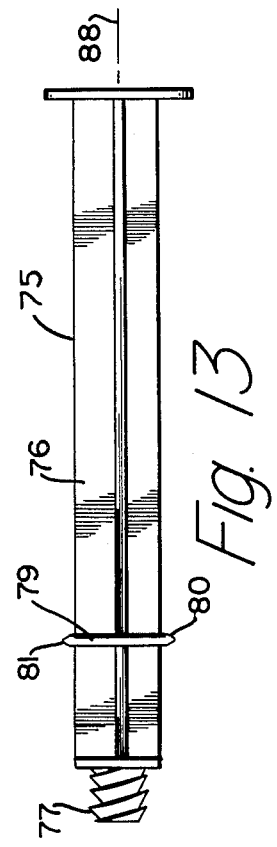
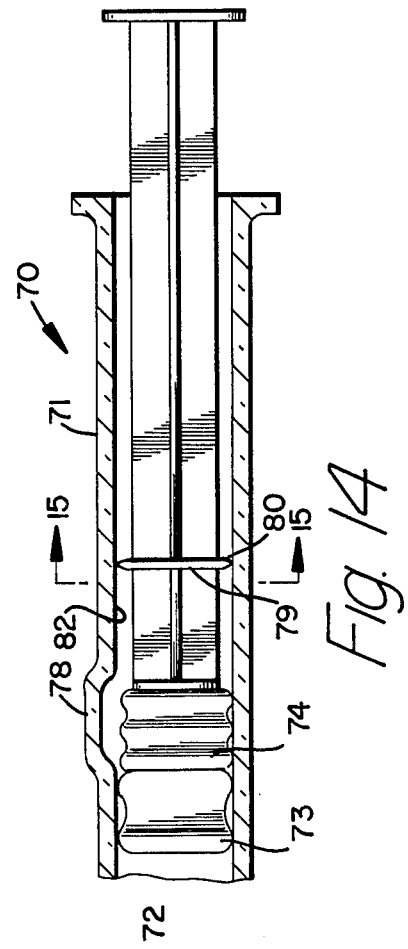
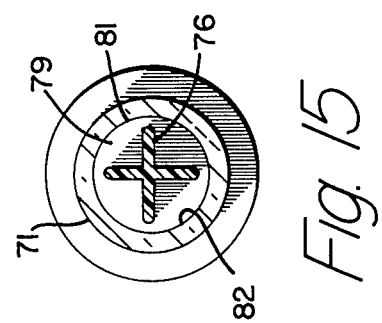

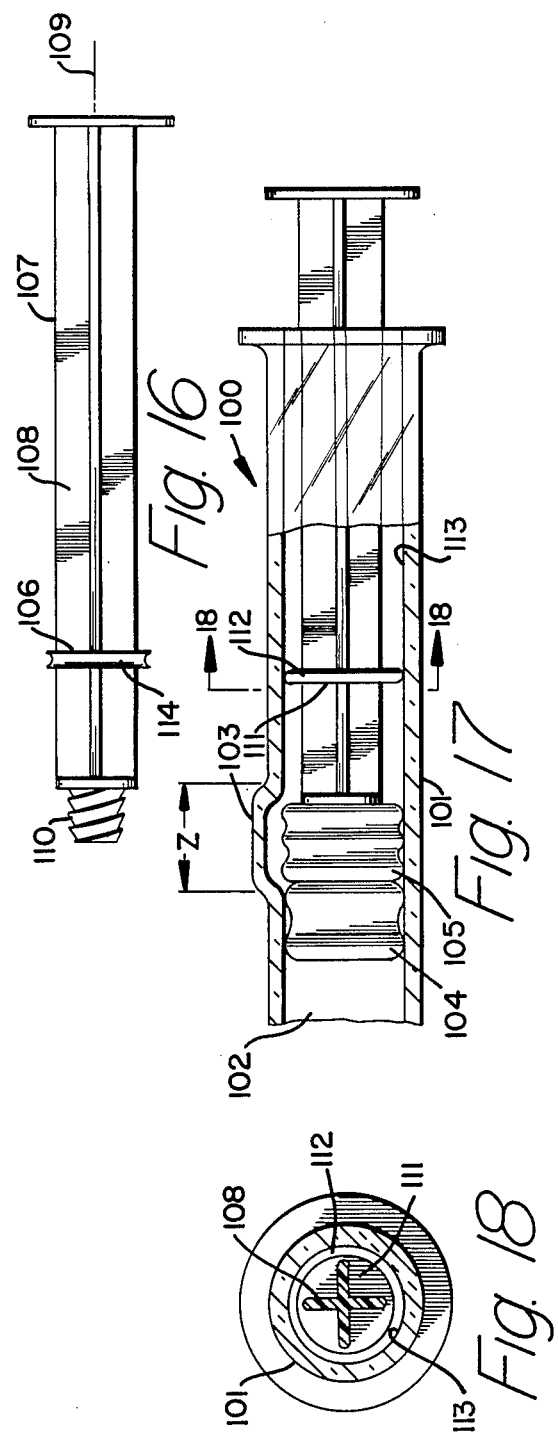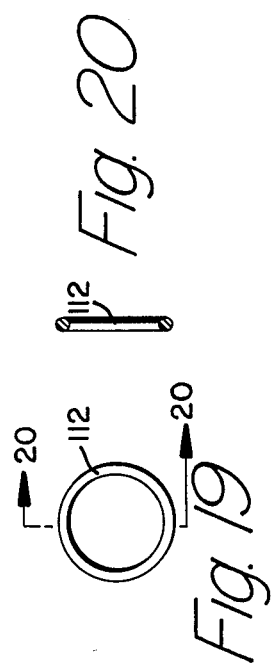

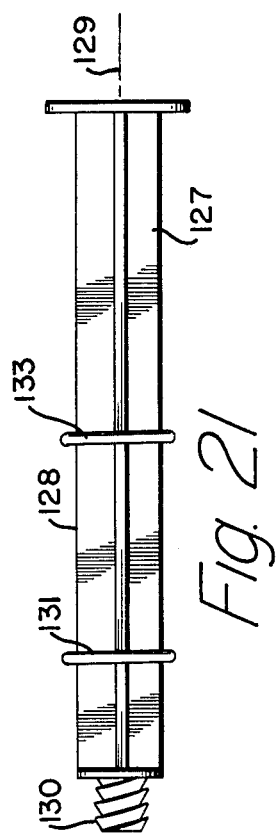
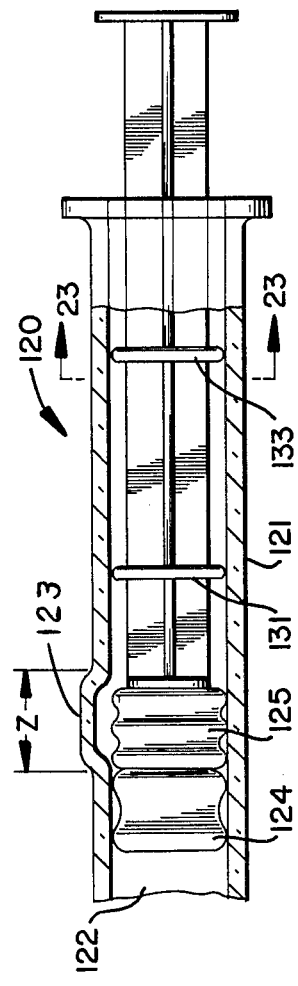
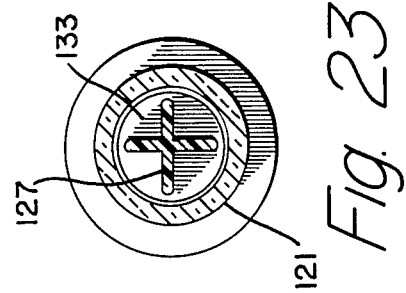

TWO-COMPONENT MEDICATION SYRINGE ASSEMBLY

BACKGROUND OF THE INVENTION

1. Field of the Invention

The present invention relates to a syringe and more particularly concerns a two-component medication syringe.

2. Description of the Prior Art

Some injectable medications have rapid loss of potency when they are in their ready-to-use form. In order to protect against the short shelf life of these medications, many of them are supplied in two components, and they are mixed at the time of use. Two-component medication is commonly available in two vials with pierceable stoppers. A first vial typically contains sterile water and the second vial contains the active ingredients which may be in lyophilized form. To prepare the medication for use, the user pierces the stopper of the vial containing the water with a sterile syringe and needle assembly and withdraws the water into the syringe. The needle is then removed from the first vial and inserted into the second vial. Water is injected into this vial to mix with the lyophilized medication. The mixed medication is then withdrawn into the syringe for injection. When the injection is to be made into a vein, it is common practice to insert the needle into the patient and to withdraw the plunger rod slightly from the syringe barrel. If the needle is in a vein, a slight amount of blood will be drawn into the syringe. The visual sighting of the blood verifies that the needle is in a vein. This procedure is called the vein indication test. Also, when injection of medication into a vein or artery is not desirable, the vein indication test can be used to assure that the hypodermic needle is not in a vein or artery.

The above recited known components present problems with respect to sterility since only the interior of the medication vial is sterile and bacteria from the exterior of the vials and the environment may be introduced into the medication during the mixing procedure. Also, at the areas where the cylindrical surfaces of the lumen of the hypodermic needle intersect the planes of its ground point, there are formed sharp edges that can potentially cut pieces of the rubber vial stopper away as the needle penetrates therein. These pieces of rubber represent a potential problem if they pass along with the liquid medication into the patient's body. Further, cost is high since two separate sterile containers and a sterile syringe are normally required.

Brown (U.S. Pat. No. 2,607,344) teaches placing both components of the medication in a glass tube where the components are separated by a stopper with a piston stopper sealing the end of the tube containing a liquid component and a flanged pierceable stopper sealing the end of the tube containing a powder component. Also, within the powder containing compartment, bounded by the stopper and the pierceable stopper, there is a longitudinally positioned groove projecting radially outwardly enlarging the inside diameter of the glass tubing. The groove is longer than the stopper so that when the stopper is positioned within the section of the tube containing the groove, liquid can flow around the stopper through the groove. Also provided is a separate barrel having an open proximal end adapted to accept the glass tube assembly and a distal end with a wall containing a cannula with opposed points. One end of the cannula projects into the barrel, and the other end projects outwardly away from the distal end of the barrel. In use, the tube assembly is inserted into the barrel so that the portion of the cannula inside the barrel penetrates the pierceable stopper establishing fluid communication between the interior of the tube and the atmosphere. Then the piston stopper is forced inwardly pushing the liquid component of the medication and the stopper toward the distal end of the barrel. When the stopper is positioned within the bypass, the liquid component flows around the stopper through the bypass to mix with the powder component. To perform the vein indication test, the tube is withdrawn to terminate fluid communication with the cannula and then the outwardly facing portion of the cannula is inserted into the patient. Since the flange of the pierceable stopper is larger than the inside diameter of the barrel, further withdrawal of the tube from the barrel creates a reduced pressure zone between the exterior end of the pierceable stopper and the cannula causing blood to flow from the cannula into the barrel, outside of the tube assembly, if the cannula is lodged in a vein.

Genese, in U.S. Pat. No. 4,226,236, teaches placing a liquid diluent and a solid medicament in a syringe barrel wherein the liquid diluent is contained between two stoppers and the solid medication is contained between one of the aforementioned stoppers and a hydrophobic filter which Genese suggests will not allow liquid to pass therethrough. This syringe contains an outwardly projecting bypass on the side of the barrel. To mix the medicament and the diluent the user removes a ferrule and the closure cap on the distal end of the syringe assembly and then pushes the plunger rod, which is attached to the first stopper, inwardly. The movement of the first stopper forces the diluent and the intermediate stopper in a forward direction until the intermediate stopper is positioned in the area of the bypass, and the diluent is then forced around the intermediate stopper through the bypass and onto the solid medicament. It appears that when the diluent contacts the entire surface of the hydrophobic filter, no air or water is permitted to pass and, further, that whatever air remains in the syringe after the diluent contacts the hydrophobic filter is trapped within the syringe and cannot escape.

At this point, Genese teaches that the syringe is to be shaken to cause mixing of the two components. To use this syringe, a slidably mounted hollow piercing member is moved rearwardly to puncture the hydrophobic filter and to allow fluid communication between the interior of the syringe barrel and the interior of the hollow piercing member. The distal end of the slidable piercing member is shaped to allow attachment of a hypodermic needle assembly. With the hypodermic needle assembly attached, the remaining air and mixed medication can be expelled from the syringe.

Brown, in U.S. Pat. No. 2,717,601 teaches an ampule for use as part of a hypodermic syringe. The ampule includes a tubular ampule body with its proximal end closed by a piston-type stopper and its distal end closed by a stopper. Between the ends of the ampule body a pair of axially extending grooves is formed in the wall thereof. A floating partition stopper is contained within the bore of the ampule on the proximal side of the grooves. A quantity of liquid diluent is contained in a first compartment which is defined by the space in the tube between the piston-type stopper and the floating partition stopper. A dry medication is contained in a second compartment which is defined by the space between the floating partition stopper and the stopper. In use, the piston-type stopper is driven along the ampule to force the floating partition stopper into the area of the grooves so the liquid diluent can pass around the floating partition stopper into the second compartment to mix with the dry medicament.

Bypass-type syringes, as taught in the patents alluded to hereinabove, require the movement of a partition stopper into a bypass area, wherein a liquid component is forced by a piston stopper around the intermediate partition stopper into the forward compartment for mixing. After all of the liquid is transferred the partition stopper and the piston stopper are in contact. When the medication is finally administered the operator forces the piston stopper and the partition stopper through the area of the bypass toward the distal end of the syringe. As the partition stopper and the piston stopper pass through the bypass area there is a tendency for medication trapped in the bypass and in the spaces between the piston stopper ribs and the inside of the syringe barrel to be projected in a rearward or proximal direction toward the operator's hands and/or the syringe plunger rod. This tendency is undesirable because some medications contain spores and/or active ingredients which should not be deposited on or near the operator's hands. Also, the presence of this liquid medication is at least a nuisance compromising the cleanliness of the injection process. The tendency to propel portions of the liquid medication in a distal direction will be called "blow-back" hereinafter.

Apparatus and methods for storage, mixing and administering two-component medication have been addressed by the prior art, as alluded to above. However, there is still a need for simple, straight-forward, reliable, easily fabricated syringe assembly for storage, mixing and administering of two-component medications. It is desirable that the syringe assembly minimize contamination potential by allowing the mixing and administering steps to be performed without puncturing stoppers or other barriers within the syringe or transferring the medication components through non-sterile barriers which are exterior to the syringe assembly. It is desirable that the syringe assembly be capable of easily performing the vein indication test and that it includes structure to block or prevent medication from being discharged through the proximal end of the syringe barrel during the injection process.

SUMMARY OF THE INVENTION

The two-component syringe of the present invention comprises an elongate barrel having a chamber for retaining fluid. The distal end of the barrel has a passageway therethrough communicating with the chamber. A bypass stopper is slidably positioned in fluid-tight engagement inside the barrel. The barrel also includes a bypass means defining a bypass zone positioned along the barrel for allowing fluid to flow around the bypass stopper when the bypass stopper is positioned intermediate the ends of the barrel in the bypass zone. A stopper is slidably positioned in fluid-tight engagement inside the barrel. A rigid plunger rod having an elongate body portion engages the stopper to facilitate operation of the stopper wherein the body portion extends outwardly from the proximal end of the barrel. A barrier means is positioned on said body portion and intermediate the ends thereof. The barrier means projects outwardly from the body portion into the space between the inside wall of the barrel and the outside of the body portion for acting as a barrier for blocking the path of fluid which may be propelled in a distal direction through the bypass while the syringe is being operated. The barrier means is positioned on the body portion so that it is within the chamber when the stopper is positioned within the bypass zone, wherein the area described by the barrier means as viewed along the longitudinal axis of the plunger rod is at least about 87 percent as large as the area described by the interior of the barrel as viewed along the longitudinal axis of the barrel.

In accordance with another embodiment of the present invention, a two-component medication syringe assembly includes an elongate substantially cylindrical barrel having an interior wall defining a chamber for retaining fluid and a tip extending from a distal end of the barrel having a passageway therethrough communicating with the chamber. Closure means is releasably connected to the tip for sealing the passageway. A bypass stopper is slidably positioned in fluid-tight engagement inside the barrel. Also provided is a raised peripheral portion of the barrel serving as a bypass and defining a bypass zone. This bypass zone is longer along the longitudinal axis of the barrel than the length of the bypass stopper along the longitudinal axis of the barrel. The bypass is raised enough to allow fluid to flow around the bypass stopper when the bypass stopper is positioned within the bypass zone. Also provided is a stopper slidably positioned in fluid-tight engagement inside the barrel. The stopper is positioned further from the distal end than the bypass stopper and is capable of moving fluid from the chamber through the passageway upon its movement toward the distal end of the barrel and capable of facilitating the drawing of fluid into the chamber through the passageway upon its movement away from the distal end of the barrel. A rigid plunger rod having an elongate body portion engages the stopper to facilitate operation of the stopper. The body portion extends outwardly from the proximal end of the barrel. A plunger rod barrier flange is positioned transversely with respect to the longitudinal axis of the body portion of the plunger rod and intermediate the ends thereof. This barrier flange projects outwardly from the body portion into the space between the inside of the barrel and the outside of the body portion wherein the area described by the periphery of the barrier flange as viewed along the longitudinal axis of the plunger rod is at least about 87 percent as large as the area described by the interior wall of the barrel when viewed along the longitudinal axis of the barrel. The barrier flange acts as a barrier for blocking the path of fluid which may be propelled in a distal direction through the bypass when the syringe is being operated. The barrier flange is positioned on the body portion of the plunger rod so that the barrier flange is within the chamber when the stopper is positioned in the bypass zone. A first component of liquid medication is contained within the chamber between the bypass stopper and the stopper. The bypass stopper is positioned outside of the bypass zone adjacent to the proximal end of the bypass. A second component of medication is substantially within the chamber between the bypass stopper and the distal end of the barrel.

In accordance with the principles of the present invention, a number of advantages and objectives are obtained. The present invention provides a simple, straight-forward, reliable, easily fabricated syringe assembly for storing, mixing and administering two-component medications. The instant invention substantially eliminates contamination potential by allowing the mixing and administering steps to be performed without puncturing stoppers or other barriers within the syringe or transferring the medication components through non-sterile barriers which are exterior to the syringe assembly. The present invention provides structure to block or prevent medication from being discharged through the proximal end of the syringe barrel during the injection process.

BRIEF DESCRIPTION OF THE DRAWINGS

FIG. 3 is a cross-sectional view of the syringe assembly of FIG. 1 taken along line 3—3;

FIG. 4 is a cross-sectional view of the syringe assembly of FIG. 1 taken along line 4—4;

FIG. 5 is a partially cross-sectioned view of the syringe assembly, similar to FIG. 2, with tip cap removed, schematically showing the mixing of the two-medication components;

FIG. 6 is a cross-sectional view of the syringe assembly of FIG. 5, similar to the cross-sectional view of FIG. 3 but with the bypass stopper in the bypass zone;

FIG. 13 is a side elevation view of an alternative plunger rod for use in the two-component medication syringe assembly of the present invention;

FIG. 14 is a partially cross-sectioned view of the two-component medication syringe assembly of the present invention illustrated with the alternative plunger rod of FIG. 13;

FIG. 15 is a cross-sectional view of the two-component medication syringe assembly of FIG. 14 taken along line 15—15;

FIG. 16 is a side elevation view of another alternative plunger rod, with gasket removed, for use in the two-component medication syringe assembly of the present invention;

FIG. 17 is a partially cross-sectioned view of the two-component medication syringe assembly of the present invention illustrated with the alternative plunger rod of FIG. 16 with a sealing gasket attached;

FIG. 18 is a cross-sectional view of the two-component medication syringe assembly of FIG. 17 taken along line 18—18;

FIG. 19 is a side elevation view of the sealing gasket for use with the alternative plunger rod of FIG. 16;

FIG. 20 is a cross-sectional view of the sealing gasket of FIG. 19 taken along lines 20—20;

FIG. 21 is a side elevation view of still another alternative plunger rod for use in the two-component medication syringe assembly of the present invention;

FIG. 22 is a partially cross-sectioned view of the two-component medication syringe assembly of the present invention illustrated with the alternative plunger rod of FIG. 21;

FIG. 23 is a cross-sectional view of the two-component medication syringe assembly of FIG. 22 taken along line 23—23;

DETAILED DESCRIPTION

Figure 1:
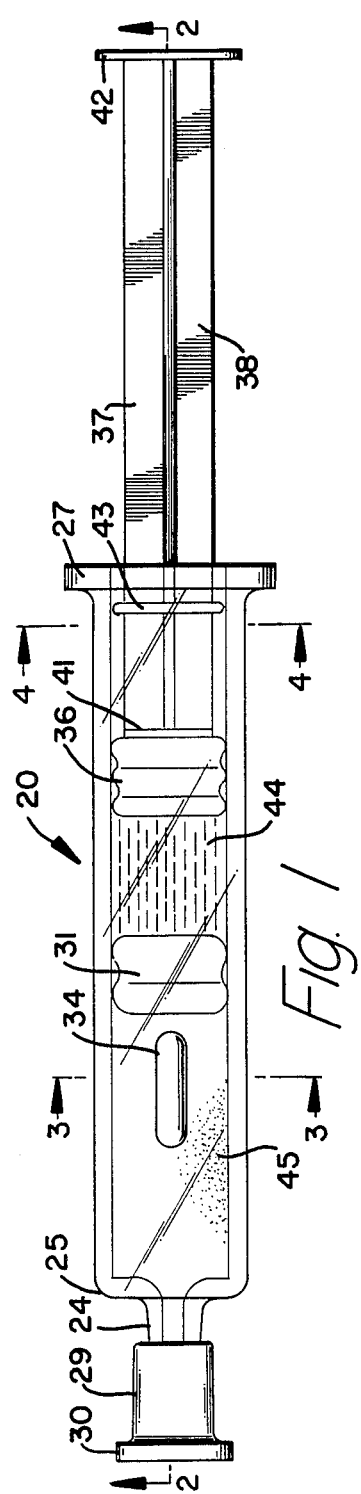
FIG. 1 is a side elevation view of the preferred two-component medication syringe assembly of the present invention.

While this invention is satisfied by embodiments in many different forms, there is shown in the drawings and will herein be described in detail preferred embodiments of the invention with the understanding that the present disclosure is to be considered as exemplary of the principles of the invention and is not intended to limit the invention to the embodiments illustrated. The scope of the invention will be measured by the appended claims and their equivalents.

Adverting to FIGS. 1 through 7, a two-component medication syringe 20 with vein indication test capacity includes an elongate substantially cylindrical barrel 21 having an interior wall 23 defining a chamber 22 for retaining fluid. A tapered tip 24 extends from a distal end 25 of the barrel and contains a passageway 26 therethrough communicating with chamber 22. For purposes of the description of the present invention, the term "distal end" is meant to refer to the end furthest from the person holding the syringe, whereas the term "proximal end" is meant to refer to the end closest to the holder of the syringe. Tapered tip 24 is adapted to accept a hypodermic needle (not shown). A closure means such as a preferably resilient tip cap 29 is releasably connected to tapered tip 24 and seals passageway 26 in an air-tight manner. Tip cap flange 30 is provided to facilitate installation and removal of the tip cap. A flange 27 is also provided at the proximal end of the barrel to facilitate handling and positioning the syringe.

A flexible bypass stopper 31 is slidably positioned in fluid-tight arrangement inside the barrel. The bypass stopper outside diameter is larger than the inside diameter of the barrel so that the bypass stopper, when introduced into the syringe barrel, is compressed enough to provide adequate pressure between the syringe barrel and the stopper to seal this interface, but yet remains slidable within the barrel under the influence of force.

Figure 2:
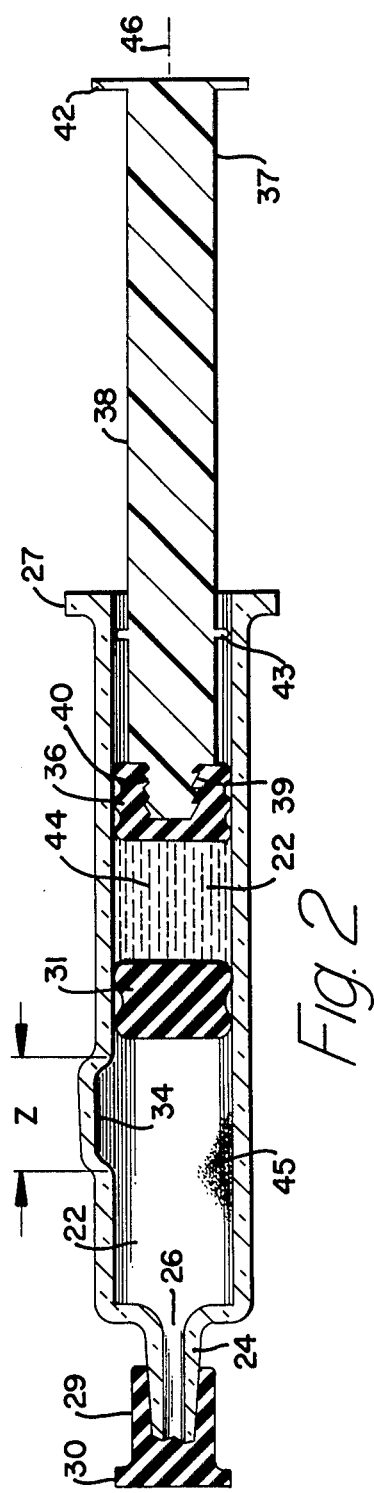
FIG. 2 is a cross-sectional view of the syringe assembly of FIG. 1 taken along line 2—2.

Syringe barrel 21 also includes a bypass 34 represented by a raised peripheral portion of the barrel extending radially outwardly and which defines bypass zone Z along the barrel. The bypass, as best illustrated in FIG. 2, effectively changes the inside diameter of the syringe barrel as measured through the bypass zone. Also, the bypass zone is longer along the longitudinal axis of the barrel than the length of bypass stopper 31 along the longitudinal axis of the barrel. As will be shown hereinafter, the bypass is large enough to allow fluid flow around the bypass stopper when the bypass stopper is positioned within the bypass zone.

A flexible stopper 36 is slidably positioned in fluid-tight engagement inside the barrel. Stopper 36 is adapted to engage a rigid plunger rod 37 having an elongate body portion 38. In the preferred embodiment, the stopper contains internal thread 39 which can engage external thread 40 on the plunger rod. The plunger rod is accessible outside of the proximal end of the barrel and is provided to move the stopper along the barrel to force fluid into or out of the chamber through the passageway. Disc-shaped plunger rod flange 42 is provided as a convenient structure for applying forces to move the plunger rod with respect to the syringe barrel. Plunger rod flange 41 is provided to supply a large surface area to transmit force from the plunger rod to the stopper, in a direction toward the stopper, without damaging the stopper.

A barrier flange 43 on elongate body portion 38 is positioned transversely with respect to a longitudinal axis 46 of body portion 38 of the plunger rod and intermediate the ends thereof. Barrier flange 43 projects outwardly from body portion 38 into the space between the inside of the barrel and the outside of the body portion wherein the area described by periphery 47 of barrier flange 43, as viewed along longitudinal axis 46 of the plunger rod, as best illustrated in FIG. 4, is desirably at least about 87 percent and preferably at least about 90 percent as large as the area described by interior wall 23 of the barrel when viewed along the longitudinal axis of the barrel. In this preferred embodiment there is a space 48 between the outside of the barrier flange and the inside of the barrel. As will be explained in more detail hereinafter barrier flange 43 acts as a barrier for blocking the path of fluid which may be propelled, or blown back, in a distal direction through the bypass while the syringe is being operated. The barrier flange is positioned on the body portion of the plunger rod so that the barrier flange is within chamber 22 when stopper 36 is positioned in the bypass zone.

The plunger rod can be installed when the syringe is assembled, or it may be provided as a separate unattached component which is engaged to the stopper at the time of use. It will be apparent to one skilled in the art that numerous constructions can be used to join a stopper and a plunger rod and that the arrangement described above is exemplary of these many possibilities. Also, it is within the purview of this invention to include a one-piece plunger rod-stopper assembly.

The preferred embodiment of the instant invention contains two components of a medication which will be mixed at the time of use. A liquid first component of medication 44 is contained within the proximal end of chamber 22 between bypass stopper 31 and stopper 36. Note that the bypass stopper is positioned outside of the bypass zone adjacent to the proximal end of the bypass. A second component of medication 45 is contained within the distal end of chamber 22 between bypass stopper 31 and the distal end of the barrel. The second component of medication may be in the form of liquid, liquid soluble powder or combinations thereof. The preferred embodiment is described with the second component being a lyophilized powder.

It should be noted that minimal force is required to move a flexible stopper along a barrel when it is well lubricated or when the liquid being injected acts as a lubricant. However, when the stopper remains in one position, even for a short period of time, the pressure exerted between the stopper and the syringe barrel tends to force liquid or lubricant out from the interface between the stopper and the barrel. As a result, the amount of force required to start the stopper moving along the syringe barrel increases dramatically. This increased force is called the breakout force. For many syringes, the breakout force is so high that if the user initially pulls on the plunger rod, it will disengage from the stopper. However, in the instant invention, stopper flange 41 allows the user to provide more force to the stopper, in the direction toward the stopper, than could be applied by the plunger rod in a direction away from the stopper, to facilitate overcoming the breakout force and moving the stopper. It can be seen that the breakout force is increased where, as with the instant invention, there are two stoppers to be moved.

Figure 7:
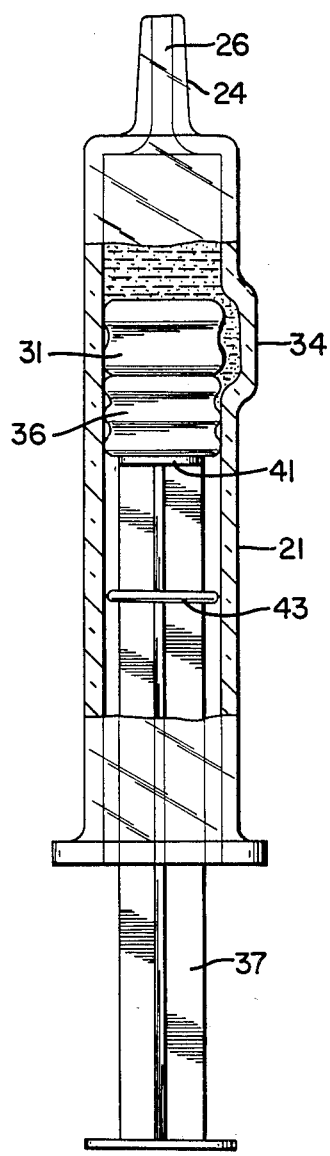
FIG. 7 is a partially cross-sectioned view of the preferred two-component medication syringe assembly showing the position of the stopper and the bypass stopper when the two-components of the medication are fully mixed.

Mixing the first and second components of the medication, as best illustrated in FIGS. 5 through 7, is accomplished by removing the tip cap and orienting the syringe so that the tip faces in an upwardly direction as more specifically illustrated in FIG. 5. The user, while holding barrel 21 in one hand, pushes plunger rod 37 firmly in a direction toward the distal end of the barrel. Once the breakout force of the stopper is overcome, stopper 36 will move toward the distal end of the syringe barrel, exerting pressure on first component 44, which in turn exerts pressure on bypass stopper 31. The stopper, first component of medication and the bypass stopper will continue to move along the barrel until the bypass stopper is positioned within the bypass zone. At this point, the pressure exerted on the liquid first component of the medication by stopper 36 will force the liquid through bypass passageway 35 between the bypass and the bypass stopper, around the bypass stopper, into the area containing the second component of medication, as best illustrated in FIG. 5. Motion of the bypass stopper toward the distal end of the syringe barrel and liquid entering the distal end of the syringe barrel, through the bypass, will displace any air contained therein and force it out of the barrel via passageway 26. Pressure on the plunger rod is continued until stopper 36 is adjacent to bypass stopper 31 and all of the liquid component is substantially in distal chamber portion 21 between the distal end of the barrel and the bypass stopper. It may now be necessary to agitate the syringe barrel to complete the mixing process. At this point, the two components of the medication are mixed, and the medication is ready for injection.

Figure 8:
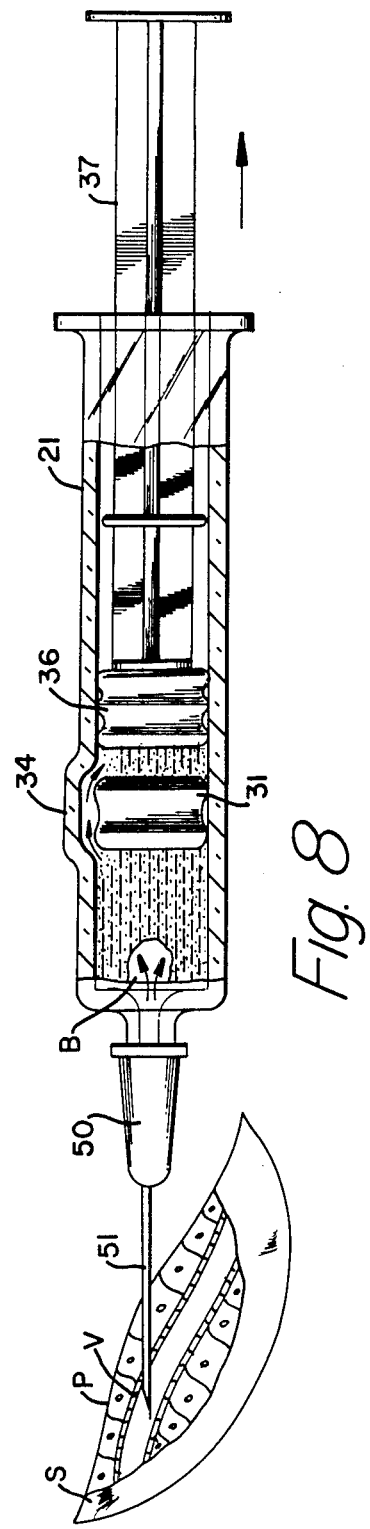
FIG. 8 is a partially cross-sectioned view of the preferred two-component medication syringe assembly, with hypodermic needle assembly attached, schematically showing the vein indication test.
Figure 9:
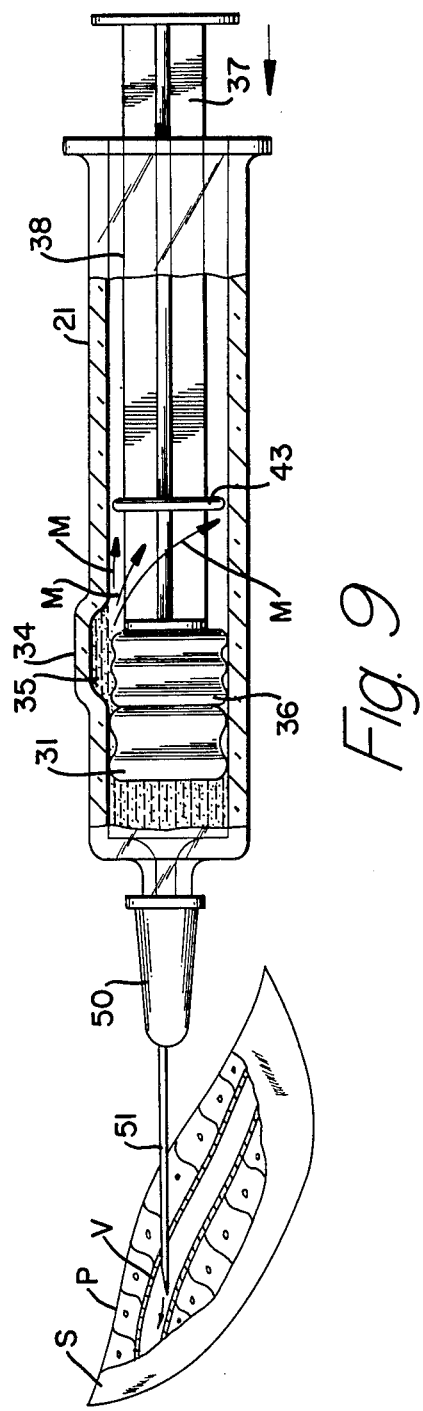
FIG. 9 is a partially cross-sectioned view of the preferred two-component medication syringe assembly, with hypodermic needle attached, schematically showing the injection of the medication and the function of the barrier flange in helping to prevent medication from being expelled through the proximal end of the syringe barrel.

Referring now to FIGS. 8 and 9, injection of the medication into the vein of patient P requires the placement of a sterile hypodermic needle assembly 50 on the tapered tip of the syringe barrel, and forcing sharp cannula 51 through the patient's skin S into the vein V. To assure that the cannula is properly inserted in the vein, the plunger rod can be drawn away from the distal end of the syringe moving the stopper 36 in that direction to create a reduced pressure zone inside the chamber which will draw blood B from the vein into the chamber. The presence of blood in the chamber will be visual evidence that the cannula is properly placed in a vein. The above described procedure for determining whether or not the cannula is properly placed in a vein is called the vein indication test.

The vein indication test capacity of the instant invention is made possible because the volume of the components of the medication, when mixed, is approximately equal to the volume defined within distal chamber portion 32 between the bypass stopper and the distal end of the barrel when the bypass stopper is within the bypass zone. This volumetric relationship allows the final precise positioning of the bypass stopper by direct contact with stopper 36 which is controlled by plunger rod 37. Most importantly, when withdrawing the plunger rod to perform the vein indication test, it is only necessary to move stopper 36 and not bypass stopper 31. Since only one stopper is being moved, the force required to move the plunger rod is less, and there is less chance that the plunger rod will become disengaged from the stopper. Also, when only one stopper is being moved, there is less chance that non-sterile air will leak around stopper 36 to the lower pressure area created within the barrel in attempting to move the stopper along the barrel in a direction toward the proximal end.

The vein indication test should also be performed when injection of medication into a vein or artery is not desirable. For example, for injecting medication intramuscularly. In this case, the sharpened cannula of the hypodermic needle, connected to the syringe assembly, is made to pierce the injection site on the patient and the plunger rod is drawn away from the distal end of the syringe, moving stopper 36 in that direction, to create a reduced pressure zone inside the chamber. The absence of blood in the chamber is visual evidence that the cannula is not improperly placed in a vein or artery.

When it is determined that the cannula is properly positioned in the patient, the medication may be injected, in the normal manner, by forcing the plunger rod toward the distal end of the barrel. The motion of plunger rod 7 forces stopper 36 along the barrel, which in turn forces any liquid that may be between stopper 36 and bypass stopper 31 through the bypass passageway into the distal chamber portion. At this point stopper 36 is in contact with bypass stopper 31 and motion of the plunger rod forces both stoppers along the barrel, thus forcing the medication through passageway 26, cannula 51 and into the patient.

As stopper 36 passes through the bypass zone, as best illustrated in FIG. 9, there is a tendency for a small amount of medication trapped in bypass passageway 35 and in the spaces between the stopper ribs and the inside of cylindrical barrel 21 to be projected or blown back in a rearward or proximal direction toward the operator's hands and/or syringe plunger rod 37. Medication being projected in a distal direction is indicated as M in FIG. 9. Barrier flange 43 positioned transversely with respect to the longitudinal axis of body portion 38 is also positioned so that it is within the chamber when stopper 36 is in the bypass zone. The barrier flange acts as a barrier to catch blown back medication which is deposited on the plunger rod and may tend to migrate along the plunger rod toward the operator's hands, and also acts as a barrier to blown back medication directed toward the interior of the barrel and toward the openings defined by the exterior of the plunger rod and the interior of the barrel. Also, medication blown back onto interior wall 23 of the barrel will be driven by gravity toward the lower portions of that wall tending to run along the syringe barrel from the lowest point. Although there is a slight clearance between barrier flange 43 and the inside of cylindrical barrel 21 the plunger rod may also tend to rest on the lower side of the barrel so that barrier flange 43 may also tend to block flow directly along the inside of the cylindrical barrel. In this preferred embodiment, the barrier flange, when viewed along longitudinal axis 46 of the plunger rod, is at least about 90 percent as large as the area described by interior wall 23 of the barrel when viewed along the longitudinal axis of the barrel.

Barrier flange 43 is an important element of the instant invention in that it helps prevent medication blown back from the bypass from being deposited on the operator's hands or the plunger rod near the operator's hands. The protection provided by the barrier flange is important because some medications contain ingredients that should not come in contact with the operator's skin. Also, the presence of this liquid medication is at least a nuisance and compromises the cleanliness of the injection process.

Figure 10:
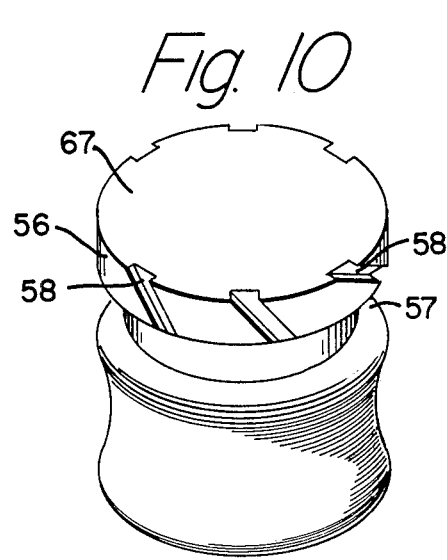
FIG. 10 is an enlarged perspective view of a bypass stopper having a bypass stopper extension.
Figure 11:
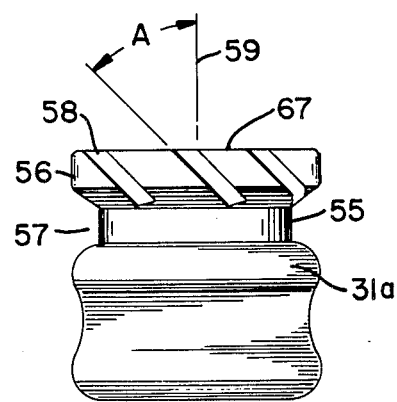
FIG. 11 is an enlarged side elevation view of the bypass stopper having a bypass stopper extension of FIG. 10.
Figure 12:
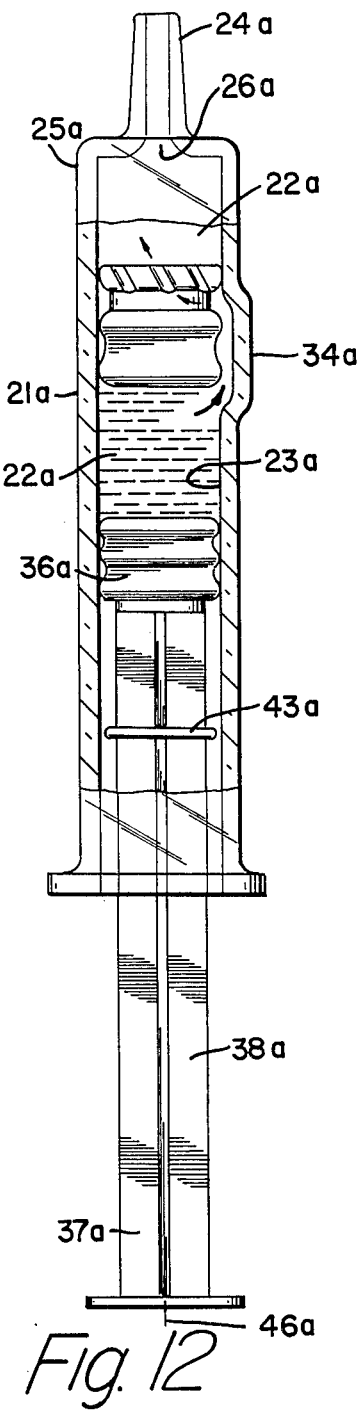
FIG. 12 is a side elevation view of an alternative two-component medication syringe assembly, with interior section partially exposed, schematically showing the mixing of the two medication components.

Referring now to FIGS. 10, 11 and 12, an alternative two-component medication syringe assembly 54 of the instant invention includes components which are substantially identical to the components of the embodiment of FIGS. 1–9. Accordingly, similar components performing similar functions will be numbered identically to those components in the embodiment of FIGS. 1–9, except that the suffix "a" will be used to identify the components of FIGS. 10–12. This alternative two-component medication syringe assembly includes an elongate substantially cylindrical barrel 21a having an interior wall 23a defining a chamber 22a for retaining fluid. A tapered tip 24a extends from distal end 25a of the barrel. Barrel 21a also includes a bypass 34a represented by a raised peripheral portion of the barrel extending radially outwardly, defining a bypass zone along the barrel. This embodiment includes a bypass stopper 31a, a stopper 36a and a plunger rod 37a. Plunger rod 37a includes an elongate body portion 38a having a threaded distal end portion (not shown) for engaging a complementary threaded portion (not shown) in stopper 36a. A plunger rod barrier flange 43a is positioned transversely with respect to longitudinal axis 46a of body portion 38a and intermediate the ends thereof. The barrier flange projects outwardly from body portion 38a into the space between the inside of the barrel and the outside of the body portion wherein the area described by the periphery of the barrier flange, as viewed along the longitudinal axis 46a of the plunger rod, is desirably at least 87 percent and preferably at least about 90 percent as large as the area described by the interior wall 23a of the barrel when viewed along the longitudinal axis of the barrel. Barrier flange 43a is positioned on the body portion of the plunger rod so that the barrier flange is within chamber 22a when stopper 36a is positioned in the bypass zone.

This alternative embodiment also includes a bypass stopper extension 55. The bypass stopper extension includes a distal extension rib 56 contacting interior wall 23a of the barrel and a recess 57 between extension rib 56 and bypass stopper 31a. This recess is capable of being in fluid communication with the bypass, as best illustrated in FIG. 12. The extension rib includes one or more grooves 58 for allowing fluid communication between the recess 57 and chamber 22a. Grooves 58 are positioned angularly with respect to the longitudinal axis 59 of the bypass stopper extension so that fluid passing through the grooves is directed angularly with respect to the longitudinal axis of the barrel, as best illustrated in FIG. 12. Grooves 58 are preferably positioned angularly with respect to longitudinal axis 59 at angle A. While not limiting the present invention thereto, angle A is preferably within the range of about 30° to 80°, with 60° being the most desirable angle. It is within the purview of this invention to include a bypass stopper extension wherein the individual grooves are at different angles with respect to the longitudinal axis. The angular orientation of the grooves causes liquid passing therethrough to be directed angularly with respect to the longitudinal axis of the barrel toward the interior wall of the barrel where the liquid tends to flow around the interior surface of the chamber causing a swirling action therein. This swirling action, facilitates the mixing of the two components of the medication. Also, the angularly positioned grooves preferably direct the liquid from the bypass away from passageway 26a of the syringe barrel to minimize the possibility of liquid being expelled through the passageway during the mixing process and before all gases are expelled from the chamber. It is also within the purview of the present invention to include a bypass stopper and a bypass stopper extension which are of a unitary one-piece construction.

In order to have vein indication test capacity with the present alternative embodiment the barrel must be proportioned so that when bypass stopper 31a is positioned in the bypass zone with recess 57 in fluid communication with the bypass and distal extension rib 56 positioned outside of the bypass zone, as best illustrated in FIG. 12, the volume defined within the chamber between distal end 67 of bypass stopper extension 55 and the distal end of the barrel is approximately the volume of the combined components of the medication.

Referring now to FIGS. 13, 14 and 15, an alternative two-component medication syringe assembly 70 of the instant invention includes an elongate substantially cylindrical barrel 71 having an inside wall 82 defining a chamber 72 and a bypass 78 represented by a raised peripheral portion of the barrel extending radially outwardly defining a bypass zone along the barrel. This embodiment also includes a bypass stopper 73, a stopper 74 and a plunger rod 75. Plunger rod includes an elongate body portion 76 having a threaded distal end portion 77 for engaging a complementary threaded portion (not shown) in stopper 74. A plunger rod barrier flange 79 is positioned transversely with respect to longitudinal axis 88 of the body portion and intermediate the ends thereof. The barrier flange projects outwardly from body portion 76 into the space between the inside of the barrel and the outside of the body portion. A resilient lip portion 80 of barrier flange 79 projects radially outwardly ending in periphery 81. The outside diameter described by the lip portion of the barrier flange is greater than the inside diameter of the barrel before the plunger rod is assembled into the barrel. Accordingly, upon assembly, the lip portion is partially deflected by the inside wall of the barrel causing a slidable engagement between the lip portion and the inside wall of the barrel. Accordingly, barrier flange 79 acts as a barrier for blocking the path of fluid which may be propelled in a distal direction through the bypass while the syringe assembly is being operated.

Adverting to FIGS. 16 through 20, another alternative two-component medication syringe assembly 100 includes an elongate barrel 101 having an interior wall 113 defining a chamber 102 for retaining medication and a raised elongate peripheral portion in the barrel serving as a bypass 103. A bypass stopper 104 is slidably positioned in fluid-tight engagement inside the barrel and a stopper 105 is also slidably positioned in fluid-tight engagement inside the barrel. A rigid plunger rod 107 includes an elongate body portion 108 defining a longitudinal axis 109 and a threaded distal end portion 110 for engaging stopper 105. Body portion 108 includes a barrier flange 111 which is positioned transversely with respect to a longitudinal axis 109 of the body portion and intermediate the ends thereof. The barrier flange projects radially outwardly from the body portion into the space between the inside of the barrel and the outside of the body portion. A resilient elastomeric gasket 112 is part of the barrier flange, and is positioned along the periphery of barrier flange base portion 106 in an annular recess 114 of the base portion. In this embodiment gasket 112 has a substantially circular cross section and is similar to the known O-ring. When gasket 112 is positioned on base portion 106 in annular recess 114, the outside diameter described by the gasket, and therefore the barrier flange, is greater than the inside diameter of the barrel. When the plunger rod is inserted into the chamber the gasket is partially compressed by the inside wall of the barrel causing a slidable engagement between the gasket and the interior wall of the barrel so that the barrier flange acts as a barrier for blocking the path of fluid which may be propelled in a distal direction through the bypass while the syringe is being operated. It should be noted that the barrier flange is positioned along elongate body portion 108 of the plunger rod so that it is within the chamber when stopper 105 is positioned in bypass zone Z. It should also be noted that the outside diameter of the base of the annular recess 114 in base portion 106 is larger than the inside diameter of the resilient elastomeric gasket so that the gasket is stretched, and in tension, when positioned in the annular recess of the base portion. This tension will cause the gasket to remain in its position with respect to base portion 106 and not be easily removed therefrom. It will be apparent to one skilled in the art that there are numerous structures and methods for obtaining a resilient portion along the periphery of a rigid body, including adhesive mounting of the resilient material, shaping the periphery of the barrier flange so that it is structurally resilient, two-shot injection molding wherein one component is a resilient material, and the other is a rigid material, and that the above structure, using a circularly shaped gasket in an annular recess, is exemplary of these many possibilities.

Referring now to FIGS. 21, 22 and 23, another alternative two-component medication syringe assembly 120 includes an elongate barrel 121 having a chamber 122 for retaining medication and a raised elongate peripheral portion serving as a bypass 123 defining a bypass zone Z. A bypass stopper 124 and a stopper 125 are slidably positioned in fluidtight engagement inside the barrel. A rigid plunger rod 127 includes an elongate body portion 128 defining a longitudinal axis 129 and a threaded distal end portion 130 for engaging stopper 125. A barrier flange 131 is positioned transversely with respect to longitudinal axis 129 of the body portion and intermediate the ends thereof. The barrier flange projects outwardly from body portion 128 into the space between the inside of the barrel and the outside of the body portion. The plunger rod also includes a second barrier flange 133 positioned transversely with respect to longitudinal axis 129 and between barrier flange 131 and the proximal end of body portion 128 so that the second barrier flange is also within the chamber when stopper 125 is positioned in the bypass zone. The area described by the periphery of the barrier flange and the second barrier flange as viewed along longitudinal axis 129 is desirably at least about 87 percent and preferably at least about 90 percent as large as the area described by the interior wall of the barrel when viewed along the longitudinal axis of the barrel. The barrier flange and the second barrier flange act as barriers for blocking the path of fluid which may be propelled in a distal direction through the bypass while the syringe is being operated. The second barrier flange, in this embodiment, provides extra protection by potentially being able to be in the path of blown back medication which is missed by the first barrier flange. Also, a second barrier flange can be used to assist in maintaining the concentricity between the plunger rod and the barrel so that the first barrier flange may have a very fragile sealing means or gasket or resilient lip, while the second barrier flange prevents the sealing means from experiencing excessive stresses. It is within the puriview of the present invention to include multiple barrier flanges wherein one or more of the flanges include the various features of the present invention such as a sealing means, a gasket, and a resilient lip portion for causing a slidable engagement between the barrier flange and the inside wall of the barrel.

Figure 25:
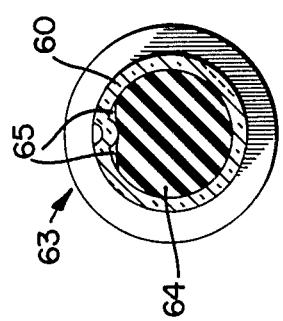
FIG. 25 is a cross-sectional view of the syringe barrel and bypass stopper of FIG. 24 taken along line 25—25.
Figure 24:
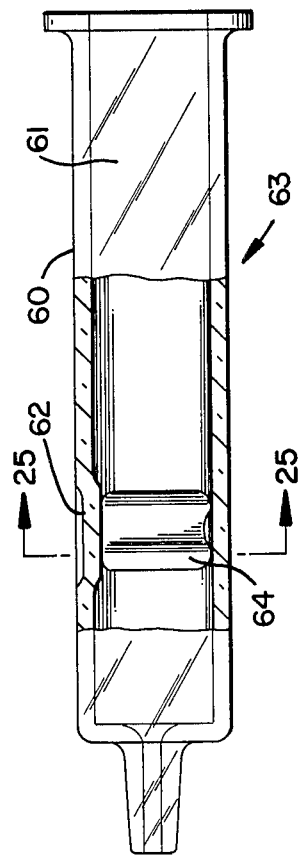
FIG. 24 is a partially cross-sectioned side elevation view of an alternative syringe barrel and bypass stopper for use in the two-component medication syringe assembly of the present invention, illustrating a radially inwardly projecting bypass.

Referring now to FIGS. 24 and 25, an alternate syringe barrel 63 for use with the two-component medication syringe assembly of the instant invention includes a barrel portion 60 having a chamber 61 for retaining fluid and a bypass 62 represented by a raised peripheral portion of the barrel extending radially inwardly defining a bypass zone along the barrel. The bypass zone is longer along the longitudinal axis of the barrel than the length of bypass stopper 64. The bypass is large enough to deflect the bypass stopper so that when the bypass stopper is in the bypass zone, liquid can flow around the bypass stopper through bypass passageways 65. Although the bypass in the various embodiments described hereinabove is substantially aligned with the longitudinal axis of the syringe barrel it is within the purview of the present invention to include syringe barrels having bypasses which are oriented at an angle with respect to the syringe barrel longitudinal axis and bypasses which are curved or curvilinearly shaped so that the distal end of the bypass is not parallel with the longitudinal axis of the syringe barrel.

Figure 26:
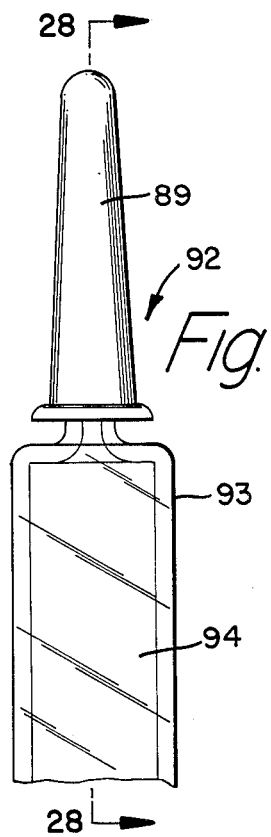
FIG. 26 is a partial side elevation view of an alternative syringe barrel and shield of the present two-component medication syringe assembly.
Figure 27:
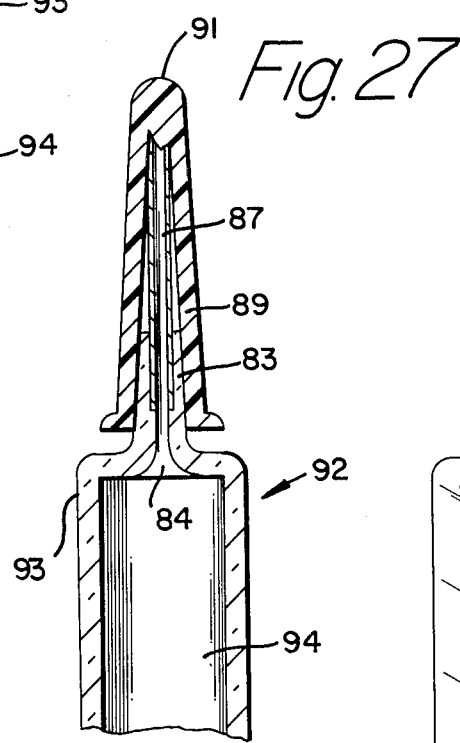
FIG. 27 is the two-component medication syringe assembly of FIG. 26 illustrating the shield removed and separated from the syringe barrel.
Figure 28:
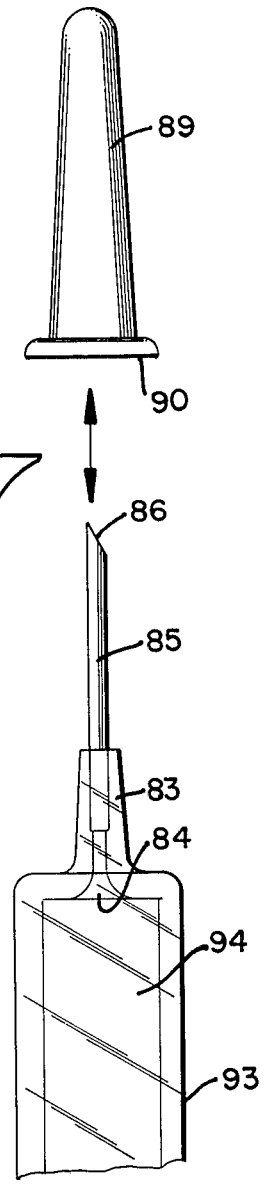
FIG. 28 is a cross-sectional view of the two-component medication syringe assembly of FIG. 26 taken along line 28—28.

Adverting to FIGS. 26, 27 and 28, another alternative syringe barrel 92 for use with the instant two-component medication syringe assembly includes barrel portion 93 having a chamber 94 for retaining fluid and a bypass (not shown). A tapered tip 83 extends from the distal end of the barrel and contains a passageway 84 therethrough communicating with chamber 94 a needle 85 with a sharp distal end 86 and a lumen 87 is fixedly held in passageway 84, via epoxy, adhesive or other suitable means, so that the lumen is in fluid communication with chamber 94. Flexible needle shield 89 has an open end 90, a closed end 91 and a receptacle therein. The needle shield is removably attached to tapered tip 83. Shield 89 is sized so that, when it is attached to the tapered tip, sharp distal end 86 is embedded in closed end 91 of the needle shield so that lumen 87, and therefore passageway 84, are sealed in an air-tight arrangement. Removal of the shield exposes needle 85 and allows flow of fluid from chamber 94 through passageway 84 and lumen 87. The above described structure eliminates the need for separate hypodermic needle assembly.

The syringe barrel may be constructed of thermoplastic material such as polypropylene or of glass. The latter material is preferred due to its transparency, low moisture vapor transmission rate and compatability with many medication formulations. A wide variety of materials are suitable for the stopper, bypass stopper, resilient gasket and tip cap with natural rubber and butyl rubber being preferred. The choice of stopper and tip cap material formulations will be highly dependent on compatability with the medication to be stored. A wide variety of rigid materials are suitable for the plunger rod with thermoplastic materials such as polypropylene, polyethylene and polystyrene being preferred. It is preferred that all medication contacting elements of the two-component medication syringe assembly be sterile when used. Accordingly, materials should be selected for compatability with the sterilization process being used.

Thus it can be seen that the present invention provides a simple straight-forward, reliable, easily fabricated syringe assembly for storage, mixing and administering of two-component medications. The instant invention minimizes contamination potential by allowing the mixing and administering steps to be performed without puncturing stoppers or transferring the medication components through surfaces which are exterior to the syringe assembly. The instant invention is capable of easily performing the vein indication test and it includes structure for blocking or preventing medication from being discharged through the proximal end of the syringe barrel during the injection process.

What is claimed is:

1. An operable two-component medication syringe assembly comprising:
   an elongate barrel having an interior wall defining a chamber for retaining medication;
   a distal end of said barrel having a passageway therethrough communicating with said chamber;
   a bypass stopper slidably positioned in fluid-tight engagement inside said barrel;
   a raised elongate peripheral portion of said barrel serving as a bypass and defining a bypass zone, said bypass zone being longer along the longitudinal axis of said barrel than the length of said bypass stopper along the longitudinal axis of said barrel, said bypass being raised enough to allow fluid flow around said bypass stopper when said bypass stopper is positioned within said bypass zone;
   a bypass stopper extension projecting outwardly from the distal end of said bypass stopper, said extension including a distal extension rib contacting said interior wall of said barrel and a recess between said extension rib and said bypass stopper, said extension rib including a groove for allowing fluid communication between said recess and said chamber, said groove being positioned angularly with respect to the longitudinal axis of said barrel so the fluid passing through said groove is directed angularly with respect to the longitudinal axis of said barrel;

a stopper slidably positioned in fluid-tight engagement inside said barrel, said stopper being positioned further from said distal end than said bypass stopper, said stopper capable of moving fluid from said chamber through said passageway upon its movement toward said distal end, said stopper capable of facilitating the drawing of fluid into said chamber through said passageway upon its movement away from said distal end;

a rigid plunger rod having an elongate body portion engaging said stopper to facilitate operation of said stopper, said body portion extending outwardly from the proximal end of said barrel; and a plunger rod barrier flange positioned transversely with respect to the longitudinal axis of said body portion and intermediate the ends thereof, said barrier flange projecting outwardly from said body portion into the space between the inside of said barrel and the outside of said body portion wherein the area described by the periphery of said barrier flange as viewed along the longitudinal axis of said plunger rod being at least about 87 percent as large as the area described by the interior wall of said barrel as viewed along the longitudinal axis of said barrel, said barrier flange acting as a barrier for blocking the path of fluid which may be propelled in a distal direction through said bypass while said syringe is being operated, said barrier flange being positioned on said body portion so that said barrier flange is within said chamber when said stopper is positioned in said bypass zone.

2. The two-component medication syringe assembly of claim 1 wherein the area described by the periphery of said barrier flange as viewed along the longitudinal axis of said plunger rod is at least about 90 percent as large as the area described by the interior wall of said barrel when viewed along the longitudinal axis of said barrel.

3. The two-component medication syringe assembly of claim 1 wherein said barrel has a substantially circularly shaped cross section.

4. The two-component medication syringe assembly of claim 4 wherein said groove is oriented at an angle within the range of about 30° to 80° with respect to the longitudinal axis of said barrel.

5. The two-component medication syringe assembly of claim 4 wherein there is a plurality of grooves all being in fluid communication with said recess.

6. The two-component medication syringe assembly of claim 1 wherein said bypass stopper and said extension are of a unitary one-piece construction.

7. The two-component medication syringe assembly of claim 1 wherein said barrier flange includes sealing means for providing slidable engagement between the periphery of said barrier flange and the interior wall of said barrel.

8. The two-component medication syringe assembly of claim 7 wherein said sealing means includes a resilient elastomeric gasket positioned along the periphery of said barrier flange so that the outside diameter described by said gasket is greater than the inside diameter of said barrel, said gasket being partially compressed by the interior wall of said barrel providing a slidable engagement between said gasket and the interior wall of said barrel.

9. The two-component medication syringe assembly of claim 8 wherein said gasket has a substantially circularly shaped cross section.

10. The two-component medication syringe assembly of claim 7 wherein said sealing means includes a resilient lip portion of said barrier flange projecting radially outwardly so that the outside diameter described by said lip portion is greater than the inside diameter of said barrel, said lip portion being partially deflected by the inside wall of said barrel causing a slidable engagement between said lip portion and the inside wall of said barrel.

11. The two-component medication syringe assembly of claim 1 further including a second barrier flange positioned transversely with respect to the longitudinal axis of said body portion and between said barrier flange and the proximal end of said body portion so that said second barrier flange is within said chamber when said stopper is positioned in said bypass zone.

12. The two-component medication syringe assembly of claim 1 further including closure means for releasably sealing said passageway.

13. The two-component medication syringe assembly of claim 12 further including a first liquid medication component in said chamber between said bypass stopper and said stopper, and a second medication component in said chamber between said bypass stopper and said distal end of said barrel, said bypass stopper being positioned outside of said bypass zone adjacent to the proximal end of said bypass.

14. The two-component medication syringe assembly of claim 13 wherein said bypass is positioned so that when said bypass stopper is within said bypass zone, the volume defined with said chamber between the distal end of said bypass stopper extension and said distal end of said barrel is approximately the volume of the combined components of the medication.

15. The two-component medication syringe assembly of claim 13 wherein said second medication component is selected from the group of medications consisting of liquid, powder or combinations thereof.

16. The two-component medication syringe assembly of claim 1 wherein said bypass is substantially straight when viewed through the longitudinal axis of said barrel.

17. The two-component medication syringe assembly of claim 4 wherein said bypass is raised in an inwardly direction from said barrel.

18. The two-component medication syringe assembly of claim 10 wherein said lip portion of said barrier flange and the remainder of said barrier flange are of integral construction.

19. The two-component medication syringe assembly of claim 1 wherein said plunger rod and said barrier flange are of integral construction.

20. A two-component syringe assembly comprising:
an elongate barrel having a chamber for retaining fluid;
a distal end of said barrel having a passageway therethrough communicating with said chamber;
a bypass stopper slidably positioned in fluid-tight engagement inside said barrel;
a bypass means defining a bypass zone positioned along said barrel for allowing fluid to flow around said bypass stopper when said bypass stopper is positioned intermediate the ends of said barrel in said bypass zone;

a bypass stopper extension projecting outwardly from the distal end of said bypass stopper, said extension including a distal extension rib contacting the inside of said barrel and a recess between said extension rib and said bypass stopper, said extension rib including a groove for allowing fluid communication between said recess and said chamber, said groove positioned angularly with respect to the longitudinal axis of said barrel so that fluid passing through said groove is directed angularly with respect to the longitudinal axis of said barrel;

a stopper slidably positioned in fluid-tight engagement inside said barrel;

a rigid plunger rod having an elongate body portion engaging said stopper to facilitate operation of said stopper, said body portion extending outwardly from the proximal end of said barrel; and a barrier means positioned on said body portion and intermediate the ends thereof, said barrier means projecting outwardly from said body portion into the space between the inside wall of said barrel and the outside of said body portion for acting as a barrier for blocking the path of fluid which may be propelled in a distal direction through said bypass while said syringe is being operated, said barrier means being positioned on said body portion so that said barrier means is within said chamber when said stopper is positioned within said bypass zone, wherein the area described by said barrier means as viewed along the longitudinal axis of said plunger rod being at least about 87 percent as large as the area described by the interior wall of said barrel as viewed along the longitudinal axis of said barrel.

21. The two-component medication syringe assembly of claim 22 wherein the area described by the periphery of said barrier flange as viewed along the longitudinal axis of said plunger rod is at least about 90 percent as large as the area described by the interior wall of said barrel when viewed along the longitudinal axis of said barrel.

22. A two-component medication syringe assembly comprising:

an elongate substantially cylindrical barrel having an interior wall defining a chamber for retaining fluid;

a tip extending from a distal end of said barrel having passageway therethrough communicating with said chamber;

closure means releasably connected to said tip for sealing said passageway;

a bypass stopper slidably positioned in fluid-tight engagement inside said barrel;

a raised peripheral portion of said barrel serving as a bypass and defining a bypass zone, said bypass zone being longer along the longitudinal axis of said barrel than the length of said bypass stopper along the longitudinal axis of said barrel, said bypass being raised enough to allow fluid flow around said bypass stopper when said bypass stopper is positioned within said bypass zone;

a bypass stopper extension projecting outwardly from the distal end of said bypass stopper, said extension including a distal extension rib contacting said interior wall of said barrel and a recess between said extension rib and said bypass stopper, said extension rib including a groove for allowing fluid communication between said recess and said chamber, said groove positioned angularly with respect to the longitudinal axis of said barrel so that fluid passing through said groove is directed angularly with respect to the longitudinal axis of said barrel;

a stopper slidably positioned in fluid-tight engagement inside said barrel, said stopper being positioned further from said distal end than said bypass stopper, said stopper capable of moving fluid from said chamber through said passageway upon its movement toward said distal end, said stopper capable of facilitating the drawing of fluid into said chamber through said passageway upon its movement away from said distal end;

a rigid plunger rod having an elongate body portion engaging said stopper to facilitate operation of said stopper, said body portion extending outwardly from the proximal end of said barrel; and a plunger rod barrier flange positioned transversely with respect to the longitudinal axis of said body portion of said plunger rod and intermediate the ends thereof, said barrier flange projecting outwardly from said body portion into the space between the inside of said barrel and the outside of said bydo portion wherein the area described by the periphery of said barrier flange as viewed along the longitudinal axis of said plunger rod being at least about 87 percent as large as the area described by the interior wall of said barrel as viewed along the longitudinal axis of said barrel, said barrier flange acting as a barrier for blocking the path of fluid which may be propelled in a distal direction through the bypass while said syringe is being operated, said barrier flange being positioned on said body portion so that said barrier flange is within said chamber when said stopper is positioned in said bypass zone;

a first component of liquid medication contained within said chamber between said bypass stopper and said stopper, said bypass stopper being positioned outside said bypass zone adjacent to the proximal end of said bypass; and a second component of medication substantially within said chamber between said bypass stopper and said distal end of said barrel.

23. The two-component medication syringe assembly of claim 22 wherein said groove is oriented at an angle within the range of about 30° to 80° with respect to the longitudinal axis of said barrel.

24. The two-component medication syringe assembly of claim 22 wherein there is a plurality of grooves all being in fluid communication with said recess.

25. The two-component medication syringe assembly of claim 22 wherein said bypass stopper and said extension are of a unitary one-piece construction.

26. The two-component medication syringe assembly of claim 22 wherein said barrier flange includes sealing means for providing slidable engagement between the periphery of said barrier flange and the interior wall of said barrel.

27. The two-component medication syringe assembly of claim 22 further including a second barrier flange positioned transversely with respect to the longitudinal axis of said body portion and between said barrier flange and the proximal end of said body portion so that said second barrier flange is within said chamber when said stopper is positioned in said bypass zone.

28. The two-component medication syringe assembly of claim 22 wherein said second medication component is selected from the group of medications consisting of liquid, powder or combinations thereof.

* * * * *